US009051231B2

(12) United States Patent
Sakyu et al.

(10) Patent No.: US 9,051,231 B2
(45) Date of Patent: Jun. 9, 2015

(54) PROCESS FOR PRODUCING 1,3,3,3-TETRAFLUOROPROPENE

(75) Inventors: Fuyuhiko Sakyu, Iruma-gun (JP); Satoshi Yoshikawa, Iruma-gun (JP); Satoru Okamoto, Fujimino (JP); Yasuo Hibino, Shiki (JP); Yoshio Nishiguchi, Iruma-gun (JP)

(73) Assignee: Central Glass Company, Limited, Ube-shi (JP)

( * ) Notice: Subject to any disclaimer, the term of this patent is extended or adjusted under 35 U.S.C. 154(b) by 11 days.

(21) Appl. No.: 13/119,658

(22) PCT Filed: Sep. 24, 2009

(86) PCT No.: PCT/JP2009/066528
§ 371 (c)(1),
(2), (4) Date: Mar. 17, 2011

(87) PCT Pub. No.: WO2010/035748
PCT Pub. Date: Apr. 1, 2010

(65) Prior Publication Data
US 2011/0172472 A1   Jul. 14, 2011

(30) Foreign Application Priority Data

Sep. 25, 2008 (JP) ................. 2008-246880
Sep. 30, 2008 (JP) ................. 2008-255666
Sep. 18, 2009 (JP) ................. 2009-217660

(51) Int. Cl.
C07C 17/20    (2006.01)
C07C 17/38    (2006.01)

(52) U.S. Cl.
CPC ............. *C07C 17/20* (2013.01); *C07C 17/38* (2013.01)

(58) Field of Classification Search
CPC ........................ C07C 17/206; C07C 17/383
USPC ......................... 570/160, 177, 179
See application file for complete search history.

(56) References Cited

U.S. PATENT DOCUMENTS

| | | | |
|---|---|---|---|
| 2,480,560 A | 8/1949 | Downing et al. | |
| 5,679,875 A | 10/1997 | Aoyama et al. | |
| 5,895,825 A | 4/1999 | Elsheikh et al. | |
| 6,111,150 A * | 8/2000 | Sakyu et al. | 570/167 |
| 6,235,951 B1 * | 5/2001 | Sakyu et al. | 570/156 |
| 2005/0033097 A1 | 2/2005 | Tung et al. | |

FOREIGN PATENT DOCUMENTS

| | | |
|---|---|---|
| CN | 1221722 A | 7/1999 |
| CN | 101028992 A | 9/2007 |
| CN | 101028993 A | 9/2007 |
| CN | 101215220 A | 7/2008 |
| EP | 0 712 828 A1 | 5/1996 |
| EP | 0 877 009 A1 | 11/1998 |
| GB | 2 439 209 A | 12/2007 |
| JP | 48 72105 A | 9/1973 |
| JP | 7-171402 A | 7/1995 |
| JP | 8-239333 A | 9/1996 |
| JP | 9-67281 A | 3/1997 |
| JP | 9-183740 A | 7/1997 |
| JP | 9-194404 A | 7/1997 |
| JP | 9-241189 A | 9/1997 |
| JP | 10-7604 | 1/1998 |
| JP | 11-140002 A | 5/1999 |
| JP | 11-180908 | 7/1999 |
| JP | 11-180908 A | 7/1999 |
| JP | 2000-63300 A | 2/2000 |
| JP | 3-158440 A | 4/2001 |
| WO | WO 2005/014512 A2 | 2/2005 |

OTHER PUBLICATIONS

R.N. Haszeldine et al., "The Addition of Free Radicals to Unsaturated Systems. Pat II*. Radical Addition to Olefins of the Type R•CH:CH₂.", 1953, pp. 1198-1207.
I.L. Knunyants et al., Izvest. Akad. Nauk S.S.S.R., Otdel. Khim. Nauk., 1960, pp. 1412-1418, No. 8, CA 55, 349f.
Martin Kotora, et al., "Selective Additions of Polyhalogenated Compounds to Chloro Substituted Ethenes Catalyzed by a Copper Complex", React. Kinet. Catal. Lett., 1991, pp. 415-419, vol. 44, No. 2.
Martin Kotora, et al., "Addition of Tetrachloromethaneto Halogenated Ethenes Catalyzed by Transition Metal Complexes", Journal of Molecular Catalysis, 1992, pp. 51-60, vol. 77, Elsevier Science Publishers B.V.
E.N. Zil'Berman, et al., "Synthesis of Liquid Telomers of Vinyl Chloride with Carbon Tetrachloride", Dzherzhinsk Scientific Research Institute of Chlorinated Organic Products and Acrylates. Translated from Zhurnal Organicheskoi Khimii, Dec. 1967, pp. 2101-2105, vol. 3, No. 12.
International Search Report (Form PCT/ISA/210) dated Dec. 28, 2009 with English Translation, along with Form PCT/ISA/237 (Eleven (11) pages).
Chinese-language Office Action dated Nov. 27, 2012 including Japanese-language translation (Six (6) pages).
Extended European Search Report dated Feb. 3, 2014 (ten (10) pages).
Miloš Hudlický, "Chemistry of Organic Fluorine Compounds," 1976, pp. 98-99, Ellis Horwood Limited.

* cited by examiner

*Primary Examiner* — Sudhakar Katakam
(74) *Attorney, Agent, or Firm* — Crowell & Moring LLP

(57) ABSTRACT

According to the first characteristic of the present invention, there is provided a production process for 1,3,3,3-tetrafluoropropene including: the first step of reacting 1,1,1,3,3-pentachloropropane with hydrogen fluoride thereby obtaining 1-chloro-3,3,3-trifluoropropene; and the second step of reacting 1-chloro-3,3,3-trifluoropropene obtained in the first step with hydrogen fluoride in a gaseous phase in the presence of a fluorination catalyst. According to the second characteristic of the present invention, there is provided a dehydration process including bringing 1,3,3,3-tetrafluoropropene containing at least water into contact with zeolite.

14 Claims, No Drawings

PROCESS FOR PRODUCING
1,3,3,3-TETRAFLUOROPROPENE

TECHNICAL FIELD

The present invention relates to a process for producing 1,3,3,3-tetrafluoropropene useful for an intermediate of medicines, agrichemicals, functional materials or pharmaceuticals, a propellant, a protective gas for magnesium production, a foaming agent and a refrigerant, and to a process for dehydrating the same.

BACKGROUND OF THE INVENTION

As a process for producing 1,3,3,3-tetrafluoropropene, there has been conventionally known a process for dehydroiodinating 1,3,3,3-tetrafluoro-1-iodopropane with an alcoholic potassium hydroxide (Non-Patent Publication 1), a process for dehydrofluorinating 1,1,1,3,3-pentafluoropropane in dibutyl ether with potassium hydroxide (Non-Patent Publication 2) or the like. Additionally, there is disclosed in Patent Publication 1 a process for dehydrofluorinating 1,1,1,3,3-pentafluoropropane with a chromium/activated carbon catalyst, while there is disclosed in Patent Publication 2 a process for obtaining 1,3,3,3-tetrafluoropropene from 1,1,1,3,3-pentafluoropropane brought into contact with a chromium-based catalyst.

On the other hand, as an example of a dehydrofluorination reaction of a general fluoroalkane compound in a gaseous phase, there is disclosed in Patent Publication 3 a process for producing a corresponding propene by bringing 1,1,1,3,3,3-hexafluoroparopane into a gaseous condition and making it contact with activated carbon or a chromium oxide catalyst, and in Patent Publication 4 a process for bringing fluoroethane into contact with activated carbon and initiating a thermal decomposition thereon.

On the other hand, as a process for producing 1-chloro-3,3,3-trifluoropropene serving as an intermediate in the present invention, there is disclosed in Patent Publication 5 a process for reacting 1,1,1,3,3-pentachloropropane with hydrogen fluoride in a gaseous phase (as a first process in a process for producing 1,1,1,3,3-pentafluoropropane) thereby obtaining 1,1,1-trifluoro-3-chloro-2-propene (1-chloro-3,3,3-trifluoropropene). Additionally, there is disclosed in Patent Publication 6 a process for reacting 1,1,1,3,3-pentachloropropane with hydrogen fluoride in the absence of a catalyst (as a first process in the process for producing 1,1,1,3,3-pentafluoropropane) thereby obtaining 1,1,1-trifluoro-3-chloro-2-propene (1-chloro-3,3,3-trifluoropropene). There are disclosed in Patent Publication 7: a process for reacting 1,1,1,3,3-pentachloropropane in a reactor, in the presence of a Lewis acid catalyst or a mixture of the Lewis acid catalyst, at a temperature lower than 150° C., and in a liquid phase (as a first process in the process for producing 1-chloro-3,3,3-trifluoropropene); a process for continuously extracting hydrogen chloride and 1-chloro-3,3,3-trifluoropropene generated in the reactor; and a process for isolating 1-chloro-3,3,3-trifluoropropene.

Additionally, in Patent Publication 8, as fluorination of a halogenated olefin, there is disclosed a process for fluorinating 1,1-dichloro-3,3,3-trifluoropropene with hydrogen fluoride in a gaseous phase in the presence of a fluorination catalyst.

Additionally, there is disclosed in Patent Publication 9 a process for reacting 1-chloro-3,3,3-trifluoropropene with hydrogen fluoride thereby obtaining 1,3,3,3-tetrafluoropropene.

In general, a product extracted from a reaction process for producing 1,3,3,3-tetrafluoropropene contains an acid component; therefore, it is necessary to conduct a step of washing with water and/or a step of washing with a basic aqueous solution.

Concerning dehydration of 1,1,1,3,3-pentafluoropropane serving as fluorinated hydrocarbon, a process for bringing it into contact with a specified zeolite (Patent Publication 10).

Concerning fluoroolefin, meanwhile, it is known that olefin having trifluoromethyl group involves a case where fluorine at vinyl position is eliminated in the presence of bases. Actually, 1,3,3,3-tetrafluoropropene is not stable in a case of coexistence with a basic compound such as amine.

Additionally, zeolite is known to be used as a catalyst for hydration reaction of olefin, and there is disclosed that alcohol is generated by a reaction between olefin and water (Patent Publication 11).

REFERENCES ABOUT PRIOR ART

Patent Publication

Patent Publication 1: Japanese Patent Application Publication No. 11-140002
Patent Publication 2: Japanese Patent Application Publication No. 2000-63300
Patent Publication 3: Japanese Patent Application Publication No. 9-67281
Patent Publication 4: U.S. Pat. No. 2,480,560
Patent Publication 5: Japanese Patent Application Publication No. 9-183740
Patent Publication 6: Japanese Patent Application Publication No. 11.180908
Patent Publication 7: International Publication No. 2005-014512
Patent Publication 8: Japanese Patent Application Publication No. 48-72105
Patent Publication 9: Japanese Patent Application Publication No. 10.7604
Patent Publication 10: Japanese Patent Application Publication No. 9-241189
Patent Publication 11: Japanese Patent Application Publication No. 7-171402

Non-Patent Publication

Non-Patent Publication 1: R. N. Haszeldine et al., J. Chem. Soc. 1953, 1199-1206; CA 48 5787f
Non-Patent Publication 2: I. L. Knunyants et al., Izvest. Akad. Nauk S.S.S.R., Otdel. Khim. Nauk. 1960, 1412-18; CA 55, 349f

SUMMARY OF THE INVENTION

A process for conducting dehydrohalogenation with potassium hydroxide as the above-mentioned Non-Patent Publication 1 and Non-Patent Publication 2 has been a process excellent in conversion ratio and selectivity; however, it has many respects difficult to be industrially applied, for example, a respect requiring a solvent, a respect requiring potassium hydroxide of a stoichiometric amount or more, and a respect significantly increasing a potassium salt formed as a result of the reaction.

Additionally, it has been a general rule that a dehydrofluorination reaction of a fluoroalkane compound in a gaseous phase is not so high in conversion ratio if considering that the reaction conditions are extremely strict. For example, in a process of Patent Publication 3 which process is conducted with activated carbon or a chromium oxide catalyst by bringing 1,1,1,3,3,3-hexafluoroparopane into a gaseous condition, the conversion ratio is about 4 to 50%, though the selectivity is quantitative.

[Chemical Formula 1]

Patent Publication 3

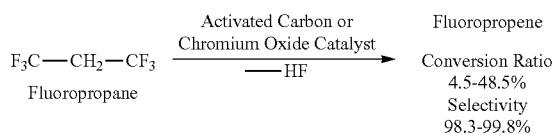

Fluoropropane — Activated Carbon or Chromium Oxide Catalyst / —HF → Fluoropropene Conversion Ratio 4.5-48.5%
Selectivity 98.3-99.8%

Additionally, in Patent Publication 4 a thermal decomposition is performed at a considerably high temperature, i.e. at about 750 to 900° C. Also in this process, the conversion ratio is about 40%.

[Chemical Formula 2]

Patent Publication 4

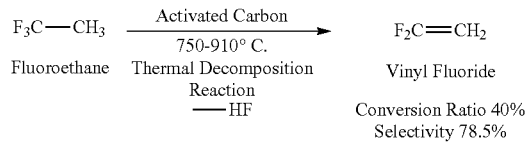

Fluoroethane — Activated Carbon / 750-910° C. Thermal Decomposition Reaction / —HF → Vinyl Fluoride Conversion Ratio 40%
Selectivity 78.5%

In order to improve the conversion ratio in the above-mentioned dehydrohalogenation, it is necessary to make the reaction conditions further strict. Additionally, from the fact that the reaction is conducted at high temperature, it is expected that a considerable difficulty is enforced in industrial production, for example, in conversion of a product into tar or charcoal, durability of a reactor and the like.

On the other hand, a selective fluorination of halogenated olefin has hitherto had a difficulty in control. For example, the process of Patent Publication 8 excellently develops the fluorination to gain the objective but forms a by-product different in fluorine atom, so that the selectivity is sometimes reduced (see below).

[Chemical Formula 3]

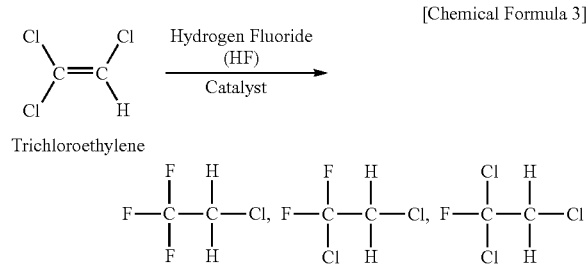

Trichloroethylene

Additionally, there have hitherto been known a fluorination reaction of a substrate having trifluoromethyl group ($CF_3$ group) in a skeleton of halogenated olefin. However, such a substrate is largely different from that having no fluorine atom also in reactivity in fluorination because of a strong electron-attracting property of fluorine atom. The process of Patent Publication 9 achieves the objective, but concurrently forms a product having a higher order structure obtained by a further developed fluorination, i.e., 1,1,1,3,3-pentafluoropropane (HFC-245fa), as a by-product. With this, the selectivity is sometimes reduced (see below).

[Chemical Formula 4]

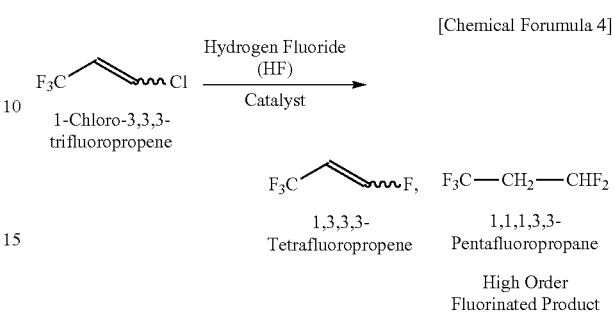

1-Chloro-3,3,3-trifluoropropene → Hydrogen Fluoride (HF) / Catalyst 1,3,3,3-Tetrafluoropropene, 1,1,1,3,3-Pentafluoropropane High Order Fluorinated Product Additionally, the process of Patent Publication 5 have a safety problem of needing hydrogen fluoride of which handling is hazardous. In addition to this, the selectivity is low and a purification by separation from hydrogen chloride to be formed, 1,1,1,3,3-pentafluoropropane, unreacted 1-chloro-3,3,3-trifluoropropene and hydrogen fluoride is so difficult as to overload devices. Therefore, this process is not necessarily preferable as an industrial production process.

As a gaseous phase fluorination catalyst for fluorinated or chlorinated and fluorinated hydrocarbon, there are known oxyfluoride of aluminum or chromium prepared by fluorinating alumina or chromia, and a carrier catalyst which carries various kinds of metals. A publication (Chemistry of Organic Fluorine Compounds: $2^{nd}$ Ed. (1976) Milos Hudlicky, p99) discusses reacting 1,1,2,2-tetrachloroethane with hydrogen fluoride and chlorine at 200° C. in the use of a catalyst in which antimony pentachloride is adsorbed on activated carbon, thereby obtaining 1,1,2-trichloro-1,2,2-trifluoroethane in 65% yield. Additionally, EP 712828 discloses that a catalyst carrying antimony pentachloride on activated carbon can fluorinate ethane with hydrogen fluoride to form 1,1,1-trifluoroethane. Either of these processes can be said to be one presenting an antimony pentachloride-carrying activated carbon as one of catalysts effective for fluorination of chlorinated ethanes.

However, when fluorinating halogenated propanes with hydrogen fluoride in the presence of the fluorination catalyst, fluorinated propenes are formed or fluorinated propene used as a raw material remains unreacted thereby raising a problem of yield reduction of the objective, as shown in a case of the gaseous phase reaction disclosed in Patent Publication 5 which case is of using chromium regarded as being apparent in fluorination activity as a catalyst.

In view of the above, there has been desired the establishment of a production process for obtaining 1,3,3,3-tetrafluoropropene, the objective of the present invention, on an industrial scale with great efficiency and high yield. This is the first challenge of the present invention.

Fluoroolefin is a fluorine-containing hydrocarbon and a compound having a double bond, and is more reactive than a saturated hydrofluorocarbon. Among these, 1,3,3,3-tetrafluoropropene is a highly reactive compound including trifluoromethyl group with a strong electron-attracting property. Particularly, decomposition of a cis isomer thereof greatly develops in the presence of a base. Meanwhile, zeolite is known as being basic in the presence of water and is well known as being attended with an intense heat generation at the early stage of water-adsorption. Therefore, it is readily inferred from analogy that some reaction is possible to develop in a case of acting zeolite on 1,3,3,3-tetrafluoropropene.

Furthermore, zeolite is also known as being useful as a catalyst for an olefin hydrating reaction as discussed in Patent Publication 11 while an effective process as a dehydration process for 1,3,3,3-tetrafluoropropene has not been known. Accordingly, the second challenge of the present invention is to provide a dehydration process in which neither decomposition nor hydrating reaction develops in the dehydration of 1,3,3,3-tetrafluoropropene.

The present inventors have eagerly made studies in order to solve the first challenge. As a result of this, they have achieved a finding that the conversion ratio and the selectivity of the objective 1,3,3,3-tetrafluoropropene is increased by using 1,1,1,3,3-pentachloropropane as the raw material and by undergoing the following two steps to result in allowing remarkably reducing the content of an unsaturated compound serving as a raw material or intermediate difficult to separate by distillation from the objective product, thereby attaining the present invention.

As a result of the present inventors' further eager studies made in order to solve the second challenge, they have achieved a finding that even 1,3,3,3-tetrafluoropropene containing a large quantity of water can be one almost bare of water content by being brought into contact with a specified zeolite, thereby reaching completion of the present invention.

According to the first characteristic of the present invention, there is provided a production process for 1,3,3,3-tetrafluoropropene which process involves an invention 1 to an invention 10 as follows. With this, the first challenge is solved.

[Invention 1]
A process for producing 1,3,3,3-tetrafluoropropene, comprising:
a first step of reacting 1,1,1,3,3-pentachloropropane with hydrogen fluoride thereby obtaining 1-chloro-3,3,3-trifluoropropene; and
a second step of reacting 1-chloro-3,3,3-trifluoropropene obtained by the first step with hydrogen fluoride in a gaseous phase and in the presence of a fluorination catalyst.

[Invention 2]
A process as discussed in Invention 1, characterized by passing 1,3,3,3-tetrafluoropropene obtained by the second step further through the following steps.
Step A: a step of removing an excessive amount of hydrogen fluoride (HF), 1-chloro-3,3,3-trifluoropropene and 1,1,1,3,3-pentafluoropropane from a reaction mixture containing 1,3,3,3-tetrafluoropropene obtained by the second step;
Step B: a step of further removing a remaining hydrogen fluoride (HF) after the step A; and
Step C: a step of removing hydrogen chloride (HCl) from 1,3,3,3-tetrafluoropropene obtained by the step B.

[Invention 3]
A process as discussed in Invention 1, characterized in that the reaction at the time of reacting 1,1,1,3,3-pentachloropropane with hydrogen fluoride to produce 1-chloro-3,3,3-trifluoropropene (the first step) is conducted in the gaseous phase and in the absence of the fluorination catalyst.

[Invention 4]
A process as discussed in Invention 3, characterized in that the reaction is conducted within a reaction pressure range of from 0.1 to 1.0 MPa and within a reaction temperature range of from 150 to 350° C.

[Invention 5]
A process as discussed in Invention 1, characterized in that the reaction at the time of reacting 1,1,1,3,3-pentachloropropane with hydrogen fluoride to produce 1-chloro-3,3,3-trifluoropropene (the first step) is conducted in a liquid phase and in the absence of the fluorination catalyst.

[Invention 6]
A process as discussed in Invention 5, characterized in that the reaction is conducted within a reaction pressure range of from 0.5 to 6.0 MPa and within a reaction temperature range of from 100 to 200° C.

[Invention 7]
A process as discussed in Invention 1, characterized in that the fluorination catalyst used when reacting 1-chloro-3,3,3-trifluoropropene with a fluorination agent in the gaseous phase and in the presence of the fluorination catalyst (the second step) is: activated carbon; activated carbon that carries oxide, fluoride, chloride, fluorinated chloride, oxyfluoride, oxychloride or oxyfluorinated chloride of one kind or two or more kinds of metals selected from chromium, titanium, aluminum, manganese, nickel, cobalt and zirconium, thereon; alumina, fluorinated alumina; aluminum fluoride; zirconia; or fluorinated zirconia.

[Invention 8]
A process as discussed in Invention 7, characterized in that the reaction is conducted within a reaction pressure range of from 0.1 to 1.0 MPa and within a reaction temperature range of from 200 to 600° C.

[Invention 9]
A process for producing trans-1,3,3,3-tetrafluoropropene, characterized by purifying 1,3,3,3-tetrafluoropropene obtained by any one of the processes of Inventions 1 to 8.

[Invention 10]
A process as discussed in any one of Inventions 1 to 9, characterized in that 1-chloro-3,3,3-trifluoropropene, cis-1,3,3,3-tetrafluoropropene and 1,1,1,3,3-pentafluoropropane contained in 1,3,3,3-tetrafluoropropene, which are separated from trans-1,3,3,3-tetrafluoropropene obtained by Invention 9, are used as the raw material of the second step again.

Though there exist a lot of literatures like Patent Publications 5 to 7 which literature relates to the process for producing 1-chloro-3,3,3-trifluoropropene by reacting 1,1,1,3,3-pentachloropropane with hydrogen fluoride as the first step of the present invention, there has not hitherto been known an example where hydrogen fluoride is reacted with 1,1,1,3,3-pentachloropropane to obtain 1-chloro-3,3,3-trifluoropropene and then the propene is reacted with hydrogen fluoride in the presence of a fluorination catalyst in a gaseous phase thereby producing 1,3,3,3-tetrafluoropropene on an industrial scale with great efficiency and high yield.

Additionally, there was also gained a finding that 1-chloro-3,3,3-trifluoropropene is obtained at a high yield by conducting the reaction in the absence of the fluorination catalyst (expressed as "noncatalytic" in the present specification) in the first step of the present invention.

Additionally, in the present invention, hydrogen chloride (HCl) is increasingly formed in a reaction system with proceeding of the reaction. There was also gained in the present invention findings that the conversion ratio and the selectivity of 1-chloro-3,3,3-trifluoropropene are improved by removing the by-product hydrogen chloride and that the objective 1,3,3,3-tetrafluoropropene is produced at a high selectivity and a high yield in the second step.

Additionally, a finding that use of a specified metal in the second step is preferable was gained.

Thus, the production process of the present invention makes it possible to product the objective compound at a yield higher than that in conventional techniques under easy reaction conditions industrially possible to perform, with which the objective 1,3,3,3-tetrafluoropropene can be produced with a high productivity without environmental load.

According to the second characteristic of the present invention, there is provided a dehydration process for 1,3,3,3-tetrafluoropropene which process involves the following (1) to (7). With this, the second challenge is solved.

(1) A process for dehydrating 1,3,3,3-tetrafluoropropene, characterized by bringing 1,3,3,3-tetrafluoropropene containing at least water into contact with zeolite.

(2) A process for dehydrating 1,3,3,3-tetrafluoropropene, as discussed in (1), in which zeolite is zeolite belonging to Faujasite genus.

(3) A process for dehydrating 1,3,3,3-tetrafluoropropene, as discussed in (1) or (2), in which zeolite is a synthetic zeolite of type 3A, 4A, 5A, 10X or 13X.

(4) A process for dehydration, as discussed in any one of (1) to (3), characterized in that 1,3,3,3-tetrafluoropropene is 1,3,3,3-tetrafluoropropane obtained by fluorinating the general formula

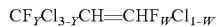

(in this formula, W is 0 or 1. Y represents an integer of from 0 to 3. However, a case of W=1 and Y=3 is excepted.) with hydrogen fluoride.

(5) A process for dehydration, as discussed in any one of (1) to (4), characterized in that 1,3,3,3-tetrafluoropropene is 1,3,3,3-tetrafluoropropene obtained by fluorinating 1-chloro-3,3,3-trifluoropropene with hydrogen fluoride.

(6) A process for dehydration, as discussed in any one of (1) to (3), characterized in that 1,3,3,3-tetrafluoropropene is 1,3,3,3-tetrafluoropropene obtained by dehydrofluorinating 1,1,1,3,3-pentafluoropropane.

(7) A process for dehydration, as discussed in any one of (1) to (6), in which 1,3,3,3-tetrafluoropropene is one of a cis isomer, a trans isomer and a mixture of these.

In the present invention, the first characteristic and the second characteristic may be combined. In other words, 1,3,3,3-tetrafluoropropene produced by the first characteristic of the present invention may be dehydrated by the second characteristic of the present invention.

DETAILED DESCRIPTION

With the production process for 1,3,3,3-tetrafluoropropene according to the present invention, there can be brought about effects of excellently developing each step under preferable reaction conditions in the use of industrially available 1,1,1,3,3-pentachloropropane as the raw material and of producing 1,3,3,3-tetrafluoropropene with a favorable yield.

Hereinafter, the first characteristic of the present invention will be further discussed in detail. It should be noted that it is omitted in the following description to specify as the first characteristic, for the purpose of simplification.

The present invention comprises a step of reacting 1,1,1,3,3-pentachloropropane with hydrogen fluoride to obtain 1-chloro-3,3,3-trifluoropropene (a first step) and a subsequent step of reacting 1-chloro-3,3,3-trifluoropropene obtained in the first step with hydrogen fluoride in a gaseous phase in the presence of a fluorination catalyst to produce 1,3,3,3-tetrafluoropropene (a second step).

This is summarized as a scheme 1 as below.

(Scheme 1)

[Chemical Formula 5]

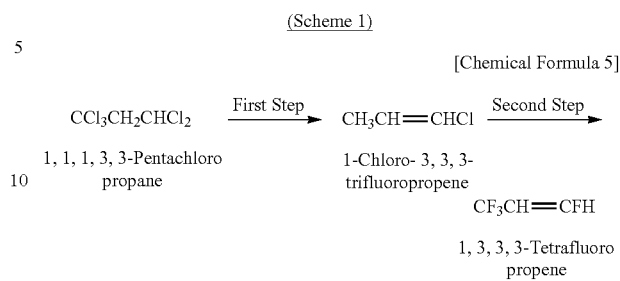

First of all, the first step will be discussed. The first step is a step of reacting 1,1,1,3,3-pentachloropropane with hydrogen fluoride to obtain 1-chloro-3,3,3-trifluoropropene.

1,1,1,3,3-Pentachloropropane, which is the starting material of the first step, can be produced by conventional processes. For example, it can be obtained by: a process of reacting vinylidene chloride with chloroform in the presence of a copper amine catalyst (M. Kotora et al., React. Kinet. Catal. Lett., 44, 2, 1991, 415.); a process of reacting carbon tetrachloride with vinyl chloride in the presence of a copper amine catalyst (M. Kotora et al., J. Mol. Catal., 77, 1992, 51.); a process of reacting carbon tetrachloride with vinyl chloride in the presence of ferrous chloride catalyst (J. Org. Chem. USSR (English Transl.), volume 3, 1967, page 2101-2105); Japanese Patent Application Publication No. 8-239333; and the like.

The present step requires a stoichiometric amount or more of hydrogen fluoride in mole ratio to 1,1,1,3,3-pentachloropropane. Under normal circumstances, hydrogen fluoride in an amount of not smaller than 3 moles relative to 1 mole of 1,1,1,3,3-pentachloropropane is enough to form 1-chloro-3,3,3-trifluoropropene, but preferably not smaller than 6 moles in order to prevent formation of tar.

The present step can be conducted in the presence of a fluorination catalyst, but it is one of the major characteristics of the present invention to conduct the reaction in the absence of the fluorination catalyst (expressed also as "noncatalytic"). Hitherto concerned problems such as dumping or recycling of the catalyst, corrosion of a reactor, and economy have been resolved by noncatalytically reacting hydrogen fluoride, with which an industrial scale production have become easy. Incidentally, the present step can be conducted in a liquid phase or a gaseous phase.

When conducting the present step in the presence of the fluorination catalyst, a catalyst used therein is to change according to reaction conditions (a liquid phase or a gaseous phase) in the present step, though particularly discussed below.

In a case where the reaction of the present step is conducted in a gaseous phase, a fluorination catalyst to be used is used upon carrying a metal compound on a carrier. Additionally, there can be used as the fluorination catalyst those obtained by fluorinating alumina, titania or stainless steel (such as fluorinated alumina), activated carbon, and the like. Examples of carrying catalyst are catalysts carrying at least one metal selected from the group consisting of aluminum, chromium, manganese, nickel and cobalt on a carrier. Usable as the carrier are alumina, fluorinated alumina, aluminum fluoride, activated carbon and the like. A preparation process for the catalyst is not particularly limited. The catalyst can be obtained by impregnating the carrier with a solution in which a soluble compound such as nitrate, chloride and the like is dissolved or by setting a carrier on which a metal salt is carried under heat after spraying and then drying thereby modifying a part or a whole of the carried metal with halogen.

Whatever processes are acceptable as a process for fluorinating the carrier; however, fluorinated alumina, for example, can be prepared by flowing hydrogen fluoride therein in the gaseous phase while heating alumina commercially available for drying use or catalyst carrier use, by spraying a hydrogen fluoride aqueous solution thereon at around room temperature, or by impregnating alumina with the aqueous solution and then drying it.

Activated carbon to be used as the catalyst or the carrier includes: plant-based one derived from lumber, charcoal, palm husk charcoal, palm kernel charcoal, plain ash or the like; coal-based one derived from peat coal, lignite, brown coal, bituminous coal, smokeless coal or the like; petroleum-based one derived from a petroleum residue, oil carbon or the like; a synthetic resin-based one such as carbonated polyvinylidene chloride; and the like. These commercially available activated carbons may be selectively used. Examples of these include: activated carbon produced from bituminous coal (granulated activated carbon BPL available from Calgon Mitsubishi Chemical Corporation); palm husk charcoal (available from Japan EnviroChemicals, Ltd. under the trade name of G2c, G2x, GS3c, GS3x, C2c, C2x or X2M, or available from Calgon Mitsubishi Chemical Corporation under the trade name of PCB); and the like, but not limited to these. Activated carbon is usually used in the form of granules concerning both shape and size, but acceptable within a normally conceivable range as far as the shape exemplified by spheres, fibers, powders, a honey-comb and the like is adaptable to the reactor. Activated carbon used in the present invention preferably has a large specific surface. A specific surface and a pore volume of activated carbon are sufficient only when they fall within a spec range of commercially available ones; however, it is preferable that they are more than 400 $m^2/g$ and more than 0.1 $cm^3/g$, respectively. Additionally, these are required only to be 800 to 3000 $m^2/g$ and 0.2 to 1.0 $cm^3/g$, respectively. Furthermore, in a case of using activated carbon as the carrier, it is preferable to immerse the activated carbon in a basic aqueous solution such as ammonium hydroxide, sodium hydroxide, potassium hydroxide and the like at around room temperature for 10 hours or more, or to conduct a pretreatment performed usually when using activated carbon as a carrier for catalyst, with acid such as nitric acid, hydrochloric acid, hydrogen fluoride and the like thereby activating the surface of the carrier while removing an ash content.

In a case of conducting the first step in a liquid phase, the separately usable as the catalyst is a high valency metal halide (discussed below) as it is, a catalyst carrying the high valency metal halide on a carrier, or activated carbon.

Examples of the high valency metal halide are antimony, tantalum, niobium, molybdenum, tin, titanium and the like, in which antimony and tantalum are preferable and antimony is the most preferable. The carried high valency metal halide is a halide represented by $SbQ_5$ (Q mutually independently represents fluorine, chlorine, bromine or iodine, which applies to the following), $TaQ_5$, $NbQ_5$, $MoQ_5$, $SnQ_4$, $TiQ_4$, or the like, and it should not be an oxyhalide. Oxygen content is to reduce the activity, so that it should be avoided.

The preparation process is not particularly limited and it is required only that the metal halide adheres to activated carbon. In a case of a compound serving as liquid at around room temperature, such as antimony pentachloride, tin tetrachloride, titanium tetrachloride and the like, it is possible to allow the liquid compound to directly adhere to activated carbon on which a pretreatment such as a treatment with a basic substance as will be discussed below, acid or hot water and dehydration treatment has been made as necessary, by a process exemplified by dropping as it is, spraying, immersion and the like. In another case of a compound serving as liquid or solid at room temperature, activated carbon is immersed in a solution obtained by dissolving the compound in a solvent to be impregnated with the solution or is subjected to a process such as spraying, thereby making the compound adhere thereto. Subsequently, the thus obtained activated carbon to which the metal compound adheres is heated or decompressed and then dried. Then, the activated carbon to which the metal compound adheres is brought into contact with hydrogen fluoride, chlorine, hydrogen chloride, chlorinated and fluorinated hydrocarbon or the like under heat, thereby preparing the catalyst. Particularly in a case of carrying antimony pentachloride, it is preferable to conduct the treatment with chlorine of not smaller than 1 equivalent at 100° C. or more, for activation of the catalyst.

In the present step, the reaction may be conducted with the addition of a solvent. However, it is possible to conduct the reaction under a condition where there is no coexistence of solvent in a reaction system, since 1,1,1,3,3-pentachloropropane used as the starting material serves as liquid at room temperature and atmospheric temperature so as to serve also as the solvent by itself. In a case of a separate addition of the solvent, the solvent is required only to be one which does not decompose the metal halide. Concrete examples thereof are: lower alcohols such as methanol, ethanol, isopropanol and the like; ethers such as methyl cellosolve, ethyl cellosolve, diethyl ether and the like; ketones such as acetone, methyl ethyl ketone and the like; aromatic compounds such as benzene, toluene, xylene and the like; esters such as ethyl acetate, butyl acetate and the like; chlorine-based solvents such as methylene chloride, chloroform, tetrachloroethylene, tetrachloroethane and the like; fluorine-based solvents such as 1,1-dichloro-1-fluoroethane, 3,3-dichloro-1,1,2,2,3-pentafluoropropane, 1,3-bis(trifluoromethyl)benzene, trifluoromethyl benzene and the like; and fluorinated propanes regarded as the starting material, intermediate or product in the present invention, such as 3-chloro-1,1,1,3-tetrafluoropropane, 3,3-dichloro-1,1,1-trifluoropropane and the like.

The solvent for antimony pentachloride, niobium pentachloride, tantalum pentachloride, molybdenum pentachloride or the like is preferably a fluorine-based solvent such as 3-chloro-1,1,1,3-tetrafluoropropane, 3,3-dichloro-1,1,1-trifluoropropane, 1,3-bis(trifluoromethyl)benzene, trifluoromethyl benzene and the like. In either of a case of using these solvent and a case of not using any solvent, it is preferable to remove substances having reactivity with halide, such as water, from solvent or a treatment system so as to carry the halide in the substantial absence of water.

The high valency metal halide used for preparing the catalyst is preferably a halide having the normally highest possible valence. Therefore, it is concretely preferable to be antimony (V: an oxidation number. This applies to the following), tin (IV), titanium (IV), niobium (V), tantalum (V) or molybdenum (V). However, the catalyst on which the high valency metal halide carried may be obtained by conducting oxidation with chlorine or the like after carrying metal halide on a carrier so as to gain the normally highest possible valence, or by conducting halogenation and/or hyperoxidation after carrying metal halide.

The metal halide used for preparing the catalyst is exemplified by antimony compounds. Examples thereof are halogenated antimony such as antimony pentachloride, antimony trichloride difluoride, antimony trichloride, antimony pentabromide, antimony tribromide, antimony pentafluoride, antimony trifluoride, antimony triiodide and the like, in which the most preferable is antimony pentachloride. Likewise, tin compound is exemplified by tin tetrachloride and tin dichloride. Titanium compound is exemplified by titanium tetrachloride and titanium trichloride. Niobium compound is exemplified by niobium pentachloride. Tantalum compound is exemplified by tantalum pentachloride. Molybdenum compound is exemplified by molybdenum pentachloride.

The carried amount of the high valency metal halide used for preparing the catalyst to be used is preferably from 0.1 to 500 parts by weight, preferably from 1 to 250 parts by weight relative to 100 parts by weight of activated carbon. Additionally, it is preferable also to adjust a catalytic activity by combining two or more kinds of metals. In this case, it is preferable to combine antimony halide (antimony pentachloride in particular) serving as the principal component with other niobium compounds (niobium pentachloride in particular), tantalum compound (tantalum pentachloride in particular), or a halide of tin, titanium, niobium, tantalum or molybdenum. There may be acceptable a case where an accessory component is not contained, so that the atomic ratio represented by accessory component metal/principal component metal may be from 50/50 to 0/100 and is preferably from 30/70 to 0/100.

The contact time of the reaction in the present step is usually from 0.1 to 300 seconds, and preferably from 1 to 60 seconds from the viewpoint of productivity.

The reaction temperature of the present step is usually from 100 to 450° C.; however, the preferable temperature range in the present step is preferably from 100 to 200° C. in liquid phase reaction while preferably from 150 to 350° C. in gaseous phase reaction. A reaction temperature of less than 100° C. lowers a reaction velocity. Concerning a reaction made in a liquid phase or a gaseous phase, the preferable temperature range is exemplified by the above-mentioned range.

The reaction pressure in the present invention usually ranges from 0.1 to 6.0 MPa; however, the preferable reaction range in the present invention is preferably from 0.5 to 6.0 MPa because it is preferable that the raw material organic substance, the intermediate and hydrogen fluoride in the liquid phase reaction serve as liquid in the reaction system. In the gaseous phase reaction, the range is preferably from 0.1 to 5.0 MPa. Incidentally, the gaseous phase reaction is actually preferably conducted at around 0.1 to 1.0 MPa.

Incidentally, the present step is the liquid phase reaction and therefore preferably conducted in a continuous or semi-continuous style. However, a batch style is also acceptable.

The reactor is required only to be one which can stand the pressure at the time of conducting the reaction at atmospheric pressure or under compression and to be formed of a material having a rust resistance against hydrogen fluoride, hydrogen chloride and the like and a heat resistance, in which the material is preferably iron, stainless steel, Hastelloy, Monel, platinum or the like. Additionally, the reactor may be formed of a material subjected to lining with these metals.

Incidentally, with proceeding of the present step, hydrogen chloride (HCl) is to be gradually generated in the reaction system; therefore, a process for extracting the generated hydrogen chloride and the objective 1-chloro-3,3,3-trifluoropropene from the reaction system is one of the preferable embodiments of the present step. In the first step, 1-chloro-3,3,3-trifluoropropene is obtained after the reaction. Then, the propene and an additional hydrogen fluoride is reacted thereby sometimes generating 1,3,3,3-tetrafluoropropene, the objective of the second step. Here, the above-mentioned removal of hydrogen chloride results in acceleration of 1,3,3,3-tetrafluoropropene formation at the later stage, thereby improving the yield thereof.

Additionally, the presence of hydrogen chloride has a disadvantage of requiring increasing the reactor in volume further than necessary, from the viewpoint of the space velocity or the contact time of the reaction substrate.

Additionally, in a case where a complete separation of hydrogen chloride is difficult in the first step, it is possible to readily separate it from the objective at a post-treatment step of the second step as discussed below.

Incidentally, in a case of causing the reaction at a pressure higher than atmospheric pressure in the present step, a reaction product (a reaction gas) is taken out of the reactor under a condition in which the reaction product itself is compressed. There is an advantage where a cooling energy needed for condensation is significantly reduced when separating hydrogen fluoride and components other than hydrogen fluoride contained in the reaction product by distillation or by gas-liquid separation, as compared with the case of conducting the present step at room temperature, since a condensation temperature is to increase under a compression condition.

Meanwhile, a very small quantity of a high boiling point organic compound generated in the present step sometimes results in activity reduction of the fluorination catalyst in the second step; therefore, it is preferable to remove a part of the organic compound and it is preferable to add a step of removing an organic compound having a relatively high boiling point. A means therefor is not particularly limited, so that a process exemplified by adsorption with activated carbon, absorption with sulfuric acid, absorption with solvent, liquid separation upon cooling, and the like is suitably employed.

A process for purifying 1-chloro-3,3,3-trifluoropropene in the present step is not particularly limited; for example, the product is washed first of all with water or an alkaline aqueous solution to remove an acidic substance such as hydrogen fluoride, followed by being drying and then subjected to distillation, with which organic impurities are removed. It is convenient to use 1-chloro-3,3,3-trifluoropropene together with a small quantity of hydrogen fluoride, as the raw material for the second step, by directly separating the organic impurities and hydrogen chloride by distillation without the washing with water or the alkaline aqueous solution.

Additionally, an excessive quantity of hydrogen fluoride generated by the present step and exhausted from the reactor together with the product may be used for reaction again by being separated from two layer of organic substances/hydrogen fluoride and recovered upon separating hydrogen chloride by distillation and the like.

Then, the second step will be discussed. The second step is a step of reacting 1-chloro-3,3,3-trifluoropropene obtained by the first step with hydrogen fluoride in a gaseous phase in the presence of a fluorination catalyst to produce 1,3,3,3-tetrafluoropropene.

1-Chloro-3,3,3-trifluoropropene, which is the starting material of the present step, is a compound having a double bond and presenting structural isomers, i.e. a cis isomer and a trans isomer. In the second step, 1-chloro-3,3,3-trifluoropropene may be the trans isomer, the cis isomer, or a mixture of the cis and trans isomers, which is not at all disadvantageous to the reaction and therefore the reaction develops excellently.

Examples of activated carbon to be used in the present step as the fluorination catalyst include: plant-based one derived from lumber, sawdust, charcoal, palm husk charcoal, palm kernel charcoal, plain ash or the like; coal-based one derived from peat coal, lignite, brown coal, bituminous coal, smokeless coal or the like; petroleum-based one derived from a petroleum residue, sulfuric acid sludge, oil carbon or the like; a synthetic resin-based one; and the like. These commercially available activated carbons may be selectively used. Examples of these include: activated carbon produced from bituminous coal (granulated activated carbon Calgon BPL (for example, available from Calgon Mitsubishi Chemical Corporation)); palm husk charcoal (PCB (available from Calgon Mitsubishi Chemical Corporation), G2x (for example, available from Japan EnviroChemicals, Ltd.); and the like. However, it will be understood that the examples are not limited to these kinds and to these makers. Additionally, these activated carbons are used in the form of granules in usual cases. Its shape and size are not particularly limited and therefore determinable, within a common knowledge, relative to the scale of the reactor.

Metal used in the present step as the fluorination catalyst is selected from metals belonging to Group 4, Group 5, Group 6, Group 7, Group 8, Group 9, Group 10, Group 11, Group 13, Group 14 and Group 15 of the periodic table. The preferable fluorination catalyst is activated carbon on which oxide, fluoride, chloride, fluorinated chloride, oxyfluoride, oxychloride or oxyfluorinated chloride of one or two or more kinds of metals selected from chromium, titanium, aluminum, manganese, nickel, cobalt and zirconium are carried. Additionally, a carrier usable therefor includes alumina, fluorinated alumina, aluminum fluoride, zirconia and fluorinated zirconia.

A preparation process for the activated carbon catalyst carrying these metals is not limited; however, the catalyst is prepared by impregnating a raw activated carbon or activated carbon previously modified with halogen by hydrogen fluoride, hydrogen chloride, chlorinated and fluorinated hydrocarbon or the like with a solution in which a soluble compound is dissolved, or by spraying the same.

The carried amount of metal is adequate to be 0.1 to 80 wt %, preferably 1 to 40 wt %. Examples of the soluble metal compound to be carried on activated carbon are nitrates, chlorides and oxides of the above-mentioned metals dissolvable in the solvent such as water, ethanol, acetone and the like. Concretely, chromic nitrate, chromic trichloride, chromic trioxide, potassium dichromate, titanium trichloride, manganese nitrate, manganese chloride, manganese dioxide, nickel nitrate, nickel chloride, cobalt nitrate, cobalt chloride and the like are usable.

It is effective to previously treat the catalyst, by whichever process it carries metal, with a fluorination agent such as hydrogen fluoride, fluorinated (and chlorinated) hydrocarbon and the like before use at a temperature of not smaller than a certain temperature, thereby preventing the change of the catalyst composition during the reaction. Additionally, it is effective for improvements in catalytic life extension, conversion ratio and reaction yield to feed oxygen, chlorine, fluorinated or chlorinated hydrocarbon or the like into the reactor during the reaction.

The reaction temperature is 200 to 600° C., preferably 300 to 500° C. A reaction temperature of lower than 200° C. slows down the reaction and therefore impractical. A reaction temperature exceeding 600° C. is not preferable, because the life span of the catalyst is shortened and the reaction proceeds rapidly but nevertheless forms a decomposition product thereby reducing the selectivity for 1,3,3,3-tetrafluoropropene.

As a process for activating the catalyst, an usual process used for reactivation of the fluorination catalyst can be adopted, in which the catalyst reduced in activity is reactivated by being suitably brought into contact with dried air, chloride, hydrogen fluoride or the like.

The reaction pressure is not particularly limited; however, the reaction is preferably conducted at 0.1 to 1.0 MPa. It is preferable to select such a condition that those who exist in the system, such as a raw material organic substance, intermediate substance and hydrogen fluoride are not liquefied in the reaction system. A contact time is usually 0.1 to 300 seconds, preferably 5 to 60 seconds.

The reactor is required only to be formed of a material having heat resistance and rust resistance against hydrogen fluoride, hydrogen chloride and the like. Stainless steel, Hastelloy, Monel, platinum and the like are preferable. Additionally, the reactor may be formed of a material subjected to lining with these metals.

In the present step, the mole ratio between 1-chloro-3,3,3-trifluoropropene to be supplied to a reaction region and hydrogen fluoride can be changed according to the reaction temperature but nevertheless 1/1 to 1/60, preferably 1/1 to 1/30. When hydrogen fluoride exceeds 60 mole times 1-chloro-3,3,3-trifluoropropene, the throughput of the organic substance is reduced and there arises a harm in separating unreacted hydrogen fluoride emitted from the reaction system from the product in the same reactor. On the other hand, hydrogen fluoride of smaller than 1 mole time decreases the conversion ratio and decreases the selectivity, which is therefore not preferable.

In the present step, it is preferable to use an excessive amount of hydrogen fluoride as compared with the stoichiometric amount, so that the unreacted hydrogen fluoride is separated from an unreacted organic substance and the product so as to be recycled into the reaction system. The separation of hydrogen fluoride and the organic substance can be conducted by a publicly known means, and will be hereinafter discussed in detail.

1,3,3,3-Tetrafluoropropene obtained by the present step is a compound having a double bond and presenting structural isomers, i.e. a cis isomer and a trans isomer. 1,3,3,3-Tetrafluoropropene obtained in the present step is considered to be a mixture of these. In addition to this, 1,3,3,3-tetrafluoropropene is often obtained as a reaction mixture containing 1-chloro-3,3,3-trifluoropropene (cis and trans isomers), 1,1,1,3,3-pentafluoropropane, an excessive amount of hydrogen fluoride, hydrogen chloride and the like.

Additionally, 1,3,3,3-tetrafluoropropene sometimes exhibits an azeotropic composition with hydrogen fluoride, so that it has been greatly difficult to remove hydrogen fluoride in particular from the mixture of these.

Here, the present step includes the following steps. More specifically, the present step undergoes:

Step A: a step of removing an excessive amount of hydrogen fluoride (HF), 1-chloro-3,3,3-trifluoropropene and 1,1,1,3,3-pentafluoropropane from the reaction mixture containing 1,3,3,3-tetrafluoropropene obtained in the second step;

Step B: a step of further removing a remaining hydrogen fluoride (HF) after the step A; and Step C: a step of removing hydrogen chloride (HCl) from 1,3,3,3-tetrafluoropropene obtained by the step B.

As discussed above, by undergoing the step A to the step C, it becomes possible to efficiently separate hydrogen fluoride from the organic substance containing 1,3,3,3-tetrafluoropropene. Additionally, hydrogen chloride derived from the first step and contained in the propene is also removed, thereby achieving the improvement in propene's purity.

In the step A, an operation such as separation by distillation was performed on the reaction mixture containing 1,3,3,3-tetrafluoropropene, 1-chloro-3,3,3-trifluoropropene, 1,1,1,3,3-pentafluoropropane, an excessive amount of hydrogen fluoride, hydrogen chloride and the like, thereby separating 1,3,3,3-tetrafluoropropene, which is a low boiling point content including hydrogen chloride, and an excessive amount of hydrogen fluoride together with high boiling point contents such as unreacted 1-chloro-3,3,3-trifluoropropene, 1,1,1,3,3-pentafluoropropane and the like.

The thus separated high boiling point contents can be brought back to the second step as they are to be reused.

An agent used when removing hydrogen fluoride at the step B is not particularly limited. The separation can be achieved by forming a complex between hydrogen fluoride and potassium fluoride, sodium fluoride or the like, for instance. The complex is reacted with calcium salt such as calcium chloride, calcium hydroxide, calcium oxide, calcium carbonate and the like or with an aqueous solution of these, thereby conducting a treatment for fixing calcium fluoride ($CaF_2$) to allow removing hydrogen fluoride from the propene.

Additionally, hydrogen fluoride may be reacted with alkali metal salts or the like, such as sodium chloride, potassium chloride and the like, thereby conducting the treatment for fixing a metal fluoride salt corresponding respectively to these to remove hydrogen fluoride from the propene.

On the other hand, the use of sulfuric acid also makes it possible to greatly remove hydrogen fluoride from the propene. In the case of using sulfuric acid, the amount of sulfuric acid can be adjusted suitably by the skilled artisan since it depends on the amount of hydrogen fluoride contained in the reaction mixture. The minimum necessary amount of sulfuric acid, for instance, may be determined from the solubility of hydrogen fluoride in 100% sulfuric acid by using a graph of the solubility relative to temperature (at 30° C., for example, about 34 g of hydrogen fluoride is dissolved in 100 g of 100% sulfuric acid).

The purity of sulfuric acid is not particularly limited. However, sulfuric acid preferably has a purity of not lower than 50% and more preferably has a purity of from about 98% to 100%. Usually, a commercially available sulfuric acid for industrial use (98%) can be used.

This treatment requires only that the temperature is not so high as to liquefy the reaction product, and conducted usually from about 20° C. to about 100° C., preferably from about 25° C. to about 50° C., and more preferably from about 25° C. to about 40° C.

In a case of treating with sulfuric acid, for instance, the removed hydrogen fluoride and sulfuric acid used in the step A may be independently separated, recovered and reused. More specifically, it is possible to use this hydrogen fluoride as the starting material for the other reaction while reusing sulfuric acid in an extraction step.

Then, the step C will be discussed. From 1,3,3,3-tetrafluoropropene obtained in the step B, hydrogen chloride (HCl) contained in the propene can be removed (the step C). As a process of removing hydrogen chloride gas, whatever usual process removing hydrogen chloride contained in the organic compound can be listed. Additionally, it is also possible to remove hydrogen chloride by a combination of these; for example, in a case of using water, there is no particular limitation thereon and therefore the skilled artisan can suitably adjust the temperature, the amount and the contacting process at the time of use.

Additionally, a step of separating hydrogen fluoride can use saturated hydrochloric acid, in which case hydrogen fluoride is recovered in the form of an aqueous solution so as to be required to be separated by distillation or the like for being dehydrogenated.

Thus, 1,3,3,3-tetrafluoropropene is obtained with high purity by undergoing the step A to the step C. If a purifying operation is performed there, trans-1,3,3,3-tetrafluoropropene can be obtained with extremely high purity, selectively from 1,3,3,3-tetrafluoropropene. The purifying operation is not particularly limited. Purification is conducted by neutralization after deoxidation, washing with water, dehydration and drying with zeolite or the like, and then distillation or the like.

A distillation operation is listed as the particularly preferable embodiment, also from the viewpoint of allowing obtaining trans-1,3,3,3-tetrafluoropropene with high purity. A material of a distillation column in the distillation operation is not particularly limited. Distillation columns formed of glass or stainless steel, and those subjected to lining with tetrafluoroethylene resin, chlorotrifluoroethylene resin, vinylidene fluoride resin, PFA resin or glass at its interior. The distillation column may be filled with a filler. Distillation is accomplished at relatively low temperatures when conducted under a reduced pressure, which is convenient and therefore preferable. The number of stages of the distillation column required for conducting distillation is not particularly limited, but preferably 5 to 100 and more preferably 10 to 50.

Thus, trans-1,3,3,3-tetrafluoropropene is obtained by the distillation operation. At this time, a cis isomer thereof, i.e., cis-1,3,3,3-tetrafluoropropene, and 1-chloro-3,3,3-trifluoropropene (cis and trans isomers) are obtained as high boiling point contents. These high boiling point contents may be used again as the raw material for the second step. Reuse of the high boiling point contents is a greatly useful process also because it can reduce wastes.

Hereinafter, the first characteristic of the present invention will be more specifically discussed with reference to Examples; however, the present invention is not limited to these Examples. Here, "%" used for a composition analysis value represents "an areal %" of a composition obtained by measuring the reaction mixture directly by gas chromatography (a detector is FID unless otherwise specified).

Preparation Example 1

100 g of a crushed coconut shell-based carbon (PCB 4×10 mesh) available from Calgon Mitsubishi Chemical Corporation was immersed in 150 g of pure water. Separately, it was mixed with a solution prepared by dissolving 40 g of $CrCl_3 \cdot 6H_2O$ (a reagent chemical) in 100 g of pure water and then stirred, followed by being set aside all day and night. Thereafter, activated carbon was extracted by filtration and then calcined for 2 hours while being kept in an electric furnace of 200° C. A thus obtained chromium-carrying activated carbon was charged into a reaction tube equipped with an electric furnace and formed of a cylindrical SUS316L of 5 cm diameter and 30 cm length, followed by increasing the temperature up to 200° C. while feeding nitrogen gas. At a point when outflow of water could not be observed, hydrogen fluoride was associated with nitrogen gas and the concentration thereof was gradually increased. The reactor temperature was increased to 400° C. when a hot spot formed by hydrogen fluoride adsorbed on the charged chromium-carrying activated carbon reached the end of the outlet of the reaction tube, followed by maintaining the condition for 2 hours thereby preparing a catalyst.

Preparation Example 2

100 g of a crushed palm husk charcoal (PCB 4×10 mesh) available from Calgon Mitsubishi Chemical Corporation was immersed in 150 g of pure water. Separately, it was mixed with 200 g of 20% $TiCl_3$ aqueous solution and then stirred, followed by being set aside all day and night. Thereafter, activated carbon was extracted by filtration and then calcined for 2 hours while being kept in an electric furnace of 200° C. A thus obtained titanium-carrying activated carbon was charged into a reaction tube equipped with an electric furnace and formed of a cylindrical SUS316L of 5 cm diameter and 30 cm length, followed by increasing the temperature up to 200° C. while feeding nitrogen gas. At a point when outflow of water could not be observed, hydrogen fluoride was associated with nitrogen gas and the concentration thereof was gradually increased. The reactor temperature was increased to 400° C. when a hot spot formed by hydrogen fluoride adsorbed on the charged titanium-carrying activated carbon reached the end of the outlet of the reaction tube, followed by maintaining the condition for 2 hours thereby preparing a catalyst.

Preparation Example 3

336 g of $CrCl_3.6H_2O$ (a reagent chemical) was dissolved in pure water to be 1 L. Therein, 250 ml of granular γ-alumina having a diameter of 5 mm and a surface area of 340 $m^2$ was immersed therein and set aside all day and night. Thereafter, γ-alumina was extracted by filtration and then kept in a hot wind-circulating dryer of 100° C., followed by being set aside a further day and night. A thus obtained chromium-carrying alumina was charged into a reaction tube equipped with an electric furnace and formed of a cylindrical SUS316L of 5 cm diameter and 30 cm length, followed by increasing the temperature up to 300° C. while feeding nitrogen gas. At a point when outflow of water could not be observed, hydrogen fluoride was associated with nitrogen gas and the concentration thereof was gradually increased. The reactor temperature was increased to 450° C. when a hot spot formed by fluorination of the charged chromium-carrying alumina reached the end of the outlet of the reaction tube, followed by maintaining the condition for 1 hours thereby preparing a catalyst.

Preparation Example 4

A 1 liter glass flask was charged with 0.2 liter of granular palm husk charcoal (pelletizied "Shirasagi G2X" available from Japan EnviroChemicals, Ltd., 4 to 6 mesh) having a surface area of 1200 $m^2$/g and a pore diameter of 18 angstroms and then heated at 130 to 150° C., followed by removing water therefrom by a vacuum pump. At a point when distillate water could not be observed, nitrogen was introduced into the flask thereby bringing about atmospheric pressure.

Example 1

First Step: Production of 1-chloro-3,3,3-trifluoropropene

A pressure-resistant container having a capacity of 2000 ml and equipped with a reflux condenser tube, a pressure sensor and the like was charged with 217 g of 1,1,1,3,3-pentachloropropane (240fa) and then charged with 370 g of hydrogen fluoride, followed by setting a reactor control temperature at 160° C. and then heating up thereto. The pressure in the system grew higher together with proceeding of the reaction, due to generation of hydrogen fluoride. When the pressure exceeded 4.0 MPa at about 30 minutes later, the reflux condenser was adjusted to be 100 and a back pressure valve formed at the back of the reflux condenser was so adjusted to control the internal pressure of the reactor to 4 to 4.2 MPa.

While introducing the raw material 240fa and hydrogen fluoride in the system at 0.74 g/min under a certainly kept pressure, a reaction product, a by-product hydrogen chloride and the like were trapped out of the system by way of the back pressure valve. Then oxide gas was removed therefrom, followed by conducting recovery into a dry ice-acetone trap and then analyzing an organic substance by gas chromatography. Results thereof are shown in Table 1.

TABLE 1

| | Introduced Amount of 240fa (g/min) | HF/240fa (Mole Ratio) | Temperature of Reflux Tower (° C.) | Recovery Ratio (%) | Distillate Ratio of HF/Org (Mole Ratio) | 1233zd Selectivity (%) |
|---|---|---|---|---|---|---|
| Initial Reaction | — | 18.5 | 105 | 49.0 | — | 95.8 |
| Example 1 | 1.0 | 8.0 | 100 | 96.0 | 3.2 | 97.2 |
| Example 2 | 1.0 | 8.0 | 95 | 93.0 | 2.7 | 98.3 |
| Example 3 | 1.7 | 6.0 | 85 | 95.3 | 1.7 | 99.8 |

Note:
Whichever conversion ratio in the present invention was not smaller than 99.9%.

Second Step: Production of 1,3,3,3-tetrafluoropropene

A gaseous phase reactor (formed of SUS316L, 1-inch diameter, 30 cm length) formed having a cylindrical reaction tube equipped with an electric furnace was charged with 150 ml of the catalyst prepared in Preparation Example 1, as a gaseous phase fluorination catalyst. The temperature of the reaction tube was increased to 200° C. while feeding nitrogen gas at a flow rate of about 100 ml/min, and then hydrogen fluoride was associated with nitrogen gas at a rate of about 0.10 g/min. The temperature of the reaction tube was subsequently increased to 500° C. and maintained for 1 hour. Thereafter, the temperature of the reaction tube was decreased to 400° C. and the feeding rate of hydrogen fluoride was set to 0.15 g/min. Then, 1-chloro-3,3,3-trifluoropropene obtained in the first step was previously gasified and started to be fed into the reactor at a rate of 0.06 g/min. Because the reaction stabilized at 1 hour after the beginning of the reaction, a product gas that flowed out of the reactor was blown into water over 2 hours from this point so as to remove acid gas. Then, 6.0 g of an organic substance was trapped by a dry ice-acetone trap. Results of analyzing the trapped organic substance by gas chromatography are shown in Table 2.

TABLE 2

| | Reaction Temperature (° C.) | Fed Amount of Raw Material g/min | | Recovered Amount of Organic Substance g | Product Amount Distribution (Areal %) | | |
|---|---|---|---|---|---|---|---|
| | | CTFP | HF | | TFP | PFP | CTFP |
| Example 1 | 400 | 0.06 | 0.15 | 6.0 | 73.0 | 11.7 | 14.1 |
| Example 2 | 400 | 0.04 | 0.18 | 4.0 | 28.1 | 0.8 | 71.1 |
| Example 3 | 500 | 0.14 | 0.14 | 13.2 | 22.3 | 0.5 | 71.0 |
| Example 4 | 320 | 0.06 | 0.09 | 6.3 | 39.7 | 23.7 | 38.6 |
| Example 5 | 320 | 0.06* | 0.09 | 6.4 | 42.0 | 25.1 | 32.9 |

Introduced amount of nitrogen gas: 100 ml/min
*Raw material of Example 5: CTFP/PFP = 75/25(mol/mol)
CTFP: 1-chloro-3,3,3-trifluoropropene
PFP: 1,1,1,3,3-pentafluoropropane
TFP: 1,3,3,3-tetrafluoropropene, trans/cis = 5/1(mol/mol)
Each amount of CTFP and TFP is a total amount of trans and cis isomers.
A remainder of the product is an unknown substance.

Example 2

First Step: Production of
1-chloro-3,3,3-trifluoropropene

A preparatory step of Example 1 was repeated with the exception that the temperature of the reflux condenser was adjusted to 95° C. Thereafter, the reaction operation, the recovery operation and the analysis of Example 1 were repeated under a condition as shown in Table 1. Results thereof are shown in Table 1.

Second Step: Production of
1,3,3,3-tetrafluoropropene

The catalyst prepared in Preparation Example 2 was used on 1-chloro-3,3,3-trifluoropropene obtained in the first step. A preparatory step of Example 1 was repeated, and then the reaction operation, the recovery operation and the analysis of Example 1 were repeated under a condition as shown in Table 2. Results thereof are shown in Table 2.

Example 3

First Step: Production of
1-chloro-3,3,3-trifluoropropene

A preparatory step of Example 1 was repeated with the exceptions that the temperature of the reflux condenser was adjusted to 85 r and that 240fa was set to 1.7 g/min and hydrogen fluoride was set to 0.94 g/min. Thereafter, the reaction operation, the recovery operation and the analysis of Example 1 were repeated under a condition as shown in Table 1. Results thereof are shown in Table 1.

Second Step: Production of
1,3,3,3-tetrafluoropropene

Activated carbon was singly used on 1-Chloro-3,3,3-trifluoropropene obtained in the first step. The reaction operation, the recovery operation and the analysis of Example 1 were repeated under a condition as shown in Table 2. Results thereof are shown in Table 2.

Example 4

Second Step: Production of
1,3,3,3-tetrafluoropropene

The catalyst prepared in Preparation Example 3 was used on 1-chloro-3,3,3-trifluoropropene obtained by the same operation as the first step of Example 1. The reaction operation, the recovery operation and the analysis of Example 1 were repeated under a condition as shown in Table 2. Results thereof are shown in Table 2.

Example 5

Second Step: Production of
1,3,3,3-tetrafluoropropene

A 25 mol % mixture of 1,1,1,3,3-pentafluoropropane was used as the raw material on 1-chloro-3,3,3-trifluoropropene obtained in the same operation as the first step of Example 1. In the use of the catalyst obtained in Preparation Example 3, the reaction operation, the recovery operation and the analysis of Example 1 were repeated under a condition as shown in Table 2. Results thereof are shown in Table 2.

Example 6

First Step: Production of
1-chloro-3,3,3-trifluoropropene

A gaseous phase reactor (a first reactor: formed of SUS316L, 2.5 cm diameter, 30 cm length) formed having a cylindrical reaction tube equipped with an electric furnace was charged with 150 milliliter of activated carbon prepared in Preparation Example 4 for catalyst. The temperature of the reaction tube was increased to 200° C. while feeding nitrogen gas at a flow rate of about 160 milliliter/min, and then hydrogen fluoride was associated with nitrogen gas at a rate of about 0.2 g/min. The temperature of the reaction tube was subsequently increased to 250° C., and 1,1,1,3,3-pentachloropropane was fed into the reactor at a rate of 0.42 g/min while feeding hydrogen fluoride at a rate of 0.75 g/min. The pressure in the system was set at 0.8 MPa by adjusting a back pressure valve formed at the back of the reactor. Because the reaction stabilized at 2 hour after the beginning of the reaction, a product gas that flowed out of the reactor was blown into water to remove acid gas, and then trapped by a dry ice-acetone trap. Results of analyzing the trapped organic substance are shown in Table 3. (Incidentally, the second step was not conducted in the present example.)

TABLE 3

|  | Fed Amount (g/min) | | Reaction Temperature (° C.) | Recovery Ratio of Organic Substance g | Composition of Recovered Organic Substance (%) | | | | |
|---|---|---|---|---|---|---|---|---|---|
|  | Organic Substance | HF |  |  | CTFP (g) | CTFP (c) | PFP | TFP (t) | TFP (c) |
| Example 6 | 0.42 | 0.75 | 250 | 93.1 | 84.6 | 11.7 | 0.3 | 1.0 | 0.2 |
| Example 7 | 0.42 | 0.75 | 250 | 88.4 | 75.1 | 10.2 | 0.6 | 1.2 | 0.3 |
| Example 8 | 0.42 | 0.75 | 250 | 57.8 | 72.1 | 17.5 | 0.5 | 1.4 | 0.3 |

CTFP (t): 1-chloro-3,3,3-trifluoropropene (trans)
CTFP (c): 1-chloro-3,3,3-trifluoropropene (cis)
PFP: 1,1,1,3,3-pentafluoropropane
TFP (t): 1,3,3,3-tetrafluoropropene (trans)
TFP (c): 1,3,3,3-tetrafluoropropene (cis)
A remainder of the product is an unidentified high boiling point substance.

Example 7

First Step: Production of
1-chloro-3,3,3-trifluoropropene

A 1 liter autoclave formed of SUS316L and equipped with a reflux condenser and a stirrer was charged with 100 milliliter of activated carbon discussed in Preparation Example 4 and 0.3 mole (50.4 g) of 1,1,2,2-tetrachloroethane. Then, 1,1,1,3,3-pentachloropropane was fed into the reactor at a rate of 0.42 g/min while feeding hydrogen fluoride at a rate of 0.75 g/min, with stirring and maintaining the temperature at 180° C. The pressure in the system was increased by hydrogen chloride generated with the proceeding of the reaction, so as to be adjusted to 1 MPa by a back pressure valve formed at the back of the reactor.

Because the reaction stabilized at 3 hour after the beginning of the reaction, a product gas that flowed out of the reactor was blown into water to remove acid gas, and then trapped by a dry ice-acetone trap. Results of analyzing the trapped organic substance are shown in Table 3. (Incidentally, the second step was not conducted in the present example.)

Example 8

First Step: Production of
1-chloro-3,3,3-trifluoropropene

The reaction operation, the recovery operation and the analysis of Example 1 were repeated without using a catalyst in the reactor. Results of analysis by gas chromatography are shown in Table 3. (Incidentally, the second step was not conducted in the present example.)

Hereinafter, the second characteristic of the present invention will be further discussed in detail. It should be noted that it is omitted in the following description to specify as the second characteristic, for the purpose of simplification.

According to the process of the present invention, there is brought about an effect of removing water contained in 1,3,3,3-tetrafluoropropene without developing decomposition and hydration reaction.

Examples of zeolite used in the present invention for removing water content are Faujasite genus, Chabazite genus, Mordenite genus and the like. Faujasite genus includes natural zeolites such as Faujasite and the like, and synthetic zeolites such as: type A e.g. 3A, 4A, 5A and the like; type X e.g. 10X, 13X and the like; and type Y. Chabazite genus includes: natural zeolites such as gmelinite, erionite, levynite and the like; and synthetic zeolites such as type R, type S, type T and the like. Mordenite genus includes natural Mordenites and synthetic ones, clinoptilolite and the like.

Additionally, various kinds of modified product, such as acid-resistant grade ones, heat-resistant grade ones and the like commercially available and obtained for instance by modifying a ratio of Si/Al or by conducting a post-treatment subsequently after synthesizing or calcining zeolite, can be selectively used as each type of zeolite.

Among these, synthetic zeolites belonging to Faujasite genus are preferable, and more specifically, readily available synthetic zeolites such as 3A, 4A, 10X, 13X and the like are particularly preferable. Zeolite used in the present invention is in any form of powders, granules, pellets and the like; however, spherical or rod-like ones shaped and calcined together with a pelletizing agent such as clay, CMC and the like are preferable particularly when used in the style of a distillation column, because of its handling ease.

A process for the contact between 1,3,3,3-tetrafluoropropene and zeolite is not limited. Examples thereof are: a batch-style process in which zeolite is thrown into 1,3,3,3-tetrafluoropropene contained in a container to be brought into contact therewith stirring or no stirring; a continuous-style process in which 1,3,3,3-tetrafluoropropene is passed through a container charged with zeolite; and the like. A treatment temperature is not particularly limited but it is not preferable to conduct the treatment under a condition where the temperature is excessively high from the viewpoint of restraining a decomposition and a side reaction. The temperature thereof is preferably −50 to 60° C. and more preferably −40 to 50° C. In a case of conducting the treatment at around atmospheric pressure, it is most preferable to conduct it at −30 to 40° C. in view of the device and of maintaining the quality of 1,3,3,3-tetrafluoropropene. When exceeding 60° C., a water content-adsorbing ability of zeolite is reduced and 1,3,3,3-tetrafluoropropene is sometimes decomposed, so that it is not preferable. A treatment pressure can be selected from whether the focus of the treatment is liquid or a gaseous condition. Usually, the treatment is conducted at 0.05 to 1 MPa.

In the continuous-style process, a linear velocity of the liquid is around 1 cm/hr to 10 m/hr and preferably 2 cm/hr to 5 m/hr. A linear velocity of slower than 1 cm/hr elongates a treatment time so as not to be preferable, while that of exceeding 10 m/hr shortens a breakthrough time so as not to be preferable.

In the batch-style process, the treatment time depends on the water content, the amount of zeolite added to 1,3,3,3-tetrafluoropropene, and the treatment temperature; however, it is 1 minute to 100 hours, preferably 2 minutes to 50 hours, much more preferably 10 minutes to 10 hours. The added amount of zeolite is not particularly limited but it is preferable to set a weight ratio of zeolite/1,3,3,3-tetrafluoropropene at 0.001 to 10. A weight ratio of not larger than 0.001 requires a long period of time for the treatment. A weight ratio of not smaller than 10 does not particularly bring about technical disadvantage but nevertheless reduces a recovery ratio of the organic substance, so as not to be economically preferable.

Additionally, in a case of conducting the treatment in a gaseous condition, the temperature thereof is required not to be lower than the boiling point of 1,3,3,3-tetrafluoropropene. Therefore, the treatment is conducted at −19° C. or more, preferably 0 to 50° C., at atmospheric pressure.

1,3,3,3-Tetrafluoropropene to which the process of the present invention is applied is one at least containing water and may be associated with water. A water content after washing with water is usually around 300 to 700 ppm and the total of the water content and the associated water is 3000 ppm to 10%. However, it becomes about 2000 ppm if a water content separation step such as a mist separator is included, so that the water content is not particularly limited since it greatly depends on the presence or absence of the step. The water content in the process of the present invention can be reduced to 100 ppm or less.

At the occasion of applying the process of the present invention, washing with water and/or a basic aqueous solution is performed if the product obtained from a reaction step contains an acid component, as will be discussed below, so that one that does not contain the acid component is preferable. The product from which the acid component is removed is provided to a dehydration step of the present invention in order not to be solidified to cause a blockage at the time of being condensed at low temperatures. If the present dehydration process was further adopted after a distillation step as the final stage of a purification step, it becomes possible to reduce the water content to 1 to 50 ppm.

The process for producing 1,3,3,3-tetrafluoropropene to which the process of the present invention is applied is not particularly limited.

For example, 1,3,3,3-tetrafluoropropene can be produced by fluorinating chlorohydropropene represented by the general formula $CF_yCl_{3-y}CH=CHF_WCl_{1-W}$ (in this formula, W is 0 or 1. Y represents an integer of from 0 to 3. However, a case of W=1 and Y=3 is excepted.) with hydrogen fluoride. Examples of the above-mentioned chlorohydropropene are 1-chloro-3,3,3-trifluoropropene ($CF_3CH=CHCl$), $CF_2ClCHCHF$, $CFCl_2CH=CHF$, and the like. There has been known a process for fluorinating 1-chloro-3,3,3-trifluoropropene with hydrogen fluoride in the presence of a catalyst.

Additionally, it can be produced also by a process of defluorinating 1,1,1,3,3,-pentafluoropropane. Examples thereof are those produced by a process by using thermal decomposition and those produced by a process of conducting dehydrofluorination in the presence of hydroxide of an alkali metal (see the process discussed in "BACKGROUND OF THE INVENTION" section).

1,3,3,3-Tetrafluoropropene is a compound having a double bond and presenting a cis isomer and a trans isomer which are structure isomers. Of the above-exemplified production processes "fluorination of 1-chloro-3,3,3-trifluoropropene" and "dehydrofluorination of 1,1,1,3,3-pentafluoropropane", by whichever production process it is produced, 1,3,3,3-tetrafluoropropene is obtained in the form of a mixture of the cis isomer and the trans isomer.

The production process of reacting 1-chloro-3,3,3-trifluoropropene with hydrogen fluoride is accomplished in either a liquid phase or a gaseous phase; however, a production process where a fluorination catalyst is activated carbon or activated carbon on which a metal compound such as chromium compound is carried, in a case of conducting the production in a gaseous phase in the presence of the fluorination catalyst, will be exemplified below.

Examples of activated carbon serving as the fluorination catalyst include: plant-based one derived from lumber, sawdust, charcoal, palm husk charcoal, palm kernel charcoal, plain ash or the like; coal-based one derived from peat coal, lignite, brown coal, bituminous coal, smokeless coal or the like; petroleum-based one derived from a petroleum residue, sulfuric acid sludge, oil carbon or the like; a synthetic resin-based one; and the like. These activated carbons may be used selectively from various kinds of them which are commercially available. Examples of these include activated carbon produced from bituminous coal (for example, granulated activated carbon Calgon CAL (available from Toyo Calgon Corporation), palm husk charcoal (for example, available from Calgon Mitsubishi Chemical Corporation), and the like. However, it will be understood that the examples are not limited to these kinds and to these makers. Additionally, these activated carbons are used in the form of granules in usual cases, but its shape and size are not particularly limited and therefore determinable, within a common knowledge, relative to the scale of the reactor.

Additionally, the above-mentioned activated carbon may be activated carbon carrying oxide, fluoride, chloride, fluorinated chloride, oxyfluoride, oxychloride, oxyfluorinated chloride or the like of one kind or two or more kinds of metals selected from aluminum, chromium, manganese, nickel, cobalt and titanium.

A process for preparing these metal-carrying activated carbon catalysts is not limited; however, the catalyst can be prepared by immersing or spraying activated carbon previously modified with halogen by using hydrogen fluoride, hydrogen chloride, chlorinated and fluorinated hydrocarbon or the like with a solution in which a soluble compound of one kind or two or more kinds of metals selected from chromium, titanium, manganese, nickel and cobalt is dissolved.

A metal-carrying amount is adequately 0.1 to 80 wt %, preferably 1 to 40 wt %. The Examples of the soluble metal compound to be carried on activated carbon are nitrates, chlorides and oxides of the above-mentioned metals dissolvable in the solvent such as water, ethanol, acetone and the like. Concretely, chromic nitrate, chromic trichloride, chromic trioxide, potassium dichromate, titanium trichloride, manganese nitrate, manganese chloride, manganese dioxide, nickel nitrate, nickel chloride, cobalt nitrate, cobalt chloride and the like are usable.

It is effective to previously treat the catalyst, by whichever process it carries metal, with a fluorination agent such as hydrogen fluoride, fluorinated (and chlorinated) hydrocarbon and the like before use at a temperature of not smaller than a certain temperature, thereby preventing the change of the catalyst composition during the reaction. Additionally, it is effective for improvements in catalytic life extension, conversion ratio and reaction yield to feed oxygen, chlorine, fluorinated or chlorinated hydrocarbon or the like into the reactor during the reaction.

The reaction temperature is 200 to 600° C., preferably 300 to 500° C. When the reaction temperature is less than 200° C., the reaction is so slow as not to be practical. A reaction temperature exceeding 600° C. reduces the catalytic life, and favorably develops the reaction but nevertheless forms a decomposition product to decrease the selectivity of 1,3,3,3-tetrafluoropropene, which is therefore not preferable.

In this production process, the mole ratio of 1-chloro-3,3,3-trifluoropropene/hydrogen fluoride, which are to be fed into the reaction region, can change according to the reaction temperature but is 1/1 to 1/60, preferably 1/1 to 1/30. When hydrogen fluoride exceeds 60 mole times 1-chloro-3,3,3-trifluoropropene, the throughput of the organic substance is reduced and there arises a harm in separating unreacted hydrogen fluoride emitted from the reaction system from the product in the same reactor. On the other hand, hydrogen fluoride of smaller than 1 mole time decreases the conversion ratio and decreases the selectivity, which is therefore not preferable.

In this production process, it is preferable to use an excessive amount of hydrogen fluoride, so that the unreacted hydrogen fluoride is separated from an unreacted organic substance and the product so as to be recycled into the reaction system. The separation between hydrogen fluoride and the organic substance can be conducted by the publicly known means.

The reaction pressure is not particularly limited, but it is preferable to set it at 1 to 10 kg/cm$^2$ in view of the device. It is preferable to select such a condition that those who exist in the system, such as a raw material organic substance, intermediate substance and hydrogen fluoride are not liquefied in the reaction system. A contact time is usually 0.1 to 300 seconds, preferably 5 to 60 seconds.

The reactor is required only to be formed of a material having heat resistance and rust resistance against hydrogen fluoride, hydrogen chloride and the like. Stainless steel, Hastelloy, Monel, platinum and the like are preferable. Additionally, the reactor may be formed of a material subjected to lining with these metals.

The reaction product obtained by the above-mentioned production process is obtained as a reaction mixture containing 1,3,3,3-tetrafluoropropene (cis and trans isomers), the raw material 1-chloro-3,3,3-trifluoropropene (cis and trans isomers), an excessive amount of hydrogen fluoride, and hydrogen chloride formed by the reaction.

This reaction product contains an acid component and therefore requires an operation for removing the acid component in the purification step. More specifically, the reaction product is brought out of the reactor in a liquid or gaseous condition together with, for example, hydrogen chloride and unreacted hydrogen fluoride. Then, an excessive amount of hydrogen fluoride is removed by operations such as liquid phase separation and the like. Thereafter, the product is passed through water or a basic aqueous solution, with which the acid component is removed. This reaction product is then provided to the dehydration step.

On the other hand, 1,3,3,3-tetrafluoropropene can be produced by dehydrofluorinating 1,1,1,3,3-pentafluoropropane. Examples of reactions relating thereto include a catalytic thermal decomposition reaction and dehydrofluorination in the presence of an alkali hydroxide.

Thermal decomposition reaction is exemplified by thermal decomposition and catalytic cracking in the use of alumina, zirconia, carbon or a catalyst carrying aluminum, chromium or the like on these, but it is not limited to these. These thermal decomposition reactions can be conducted usually in a liquid phase, in a condition where the temperature is increased, under increased pressures or reduced pressures. These thermal decomposition reactions can be conducted also in the use of a solvent inert toward hydrogen fluoride, such as fluorocarbon, hydrofluorocarbon, hydrocarbon and the like, or an inert gas such as argon and nitrogen.

More specifically, there is disclosed (in Japanese Patent Application Publication No. 11-140002) one in which a mixture gas of 1,3,3,3-tetrafluoropropen and hydrogen fluoride is obtained as the reaction product by passing 1,1,1,3,3-pentafluoropropane through activated carbon carrying chromium at a temperature of 200 to 600° C. 1,3,3,3-Tetrafluoropropene is obtained as a mixture of a principal trans isomer and a cis isomer by the reaction; however, it is not particularly disadvantageous in the present invention even if the obtained is the mixture. Additionally, by passing 1,1,1,2,3,3-hexafluoropropane through activated carbon at a temperature of 430° C., a mixture gas of 1,1,1,2,3-pentafluoropropene and hydrogen fluoride is obtained as a reaction product (Japanese Patent No. 3158440).

The reaction product obtained by the above-mentioned production process is obtained as a reaction mixture containing 1,3,3,3-tetrafluoropropene (cis and trans isomers) and hydrogen fluoride formed by the reaction. An acid component is removed by passing the mixture through water or a basic aqueous solution. The reaction product from which the acid component is removed is provided to the dehydration step.

Of the above-exemplified processes, by whichever process it was made, the reaction product is brought into contact with water or the basic aqueous solution and therefore contains a corresponding water content. The water content changes according to the component of the reaction product, the temperature, the contacting process and the like; however, it is generally 300 to 700 ppm and may be higher than this when water is associated therewith. The dehydration process of the present invention can be used even in such a system, but it is preferable to previously conduct dehydrating an excessive amount of the associated water in a preliminary dehydration step such as the mist separator.

The mist separator is for removing a water content more excessive than saturation level water content associated with the product by passing the reaction product containing water at low temperatures through a double pipe charged with metal, resin, an inorganic filler or the like. With this operation, it becomes possible to adjust the water content of the reaction product to 2000 to 2500 ppm.

When applying the dehydration process of the present invention to the reaction product from which an excess of water content is reduced, it becomes possible to reduce the water content to around 10 to 100 ppm.

If the reaction product is subsequently distilled, it becomes possible to selectively obtain any isomer (a cis or trans isomer) of 1,3,3,3-tetrafluoropropene. For example, trans-1,3,3,3-tetrafluoropropene is obtained with high purity (of not less than 99%) (see Preparation Example 2).

The distillation column is not limited in material in the distillation operation; therefore, those formed of glass or stainless steel, those subjected to lining with tetrafluoroethylene resin, chlorotrifluoroethylene resin, vinylidene fluoride resin, PFA resin or glass at its interior, and the like can be used therefor. The distillation column may be filled with a filler. Distillation is accomplished at relatively low temperatures when conducted under a reduced pressure, which is convenient and therefore preferable. The number of stages of the distillation column required for conducting distillation is not particularly limited, but preferably 5 to 100 and more preferably 10 to 50.

It is possible to apply the dehydration process further to 1,3,3,3-tetrafluoropropene formed by distillation. With the dehydration process of the present invention, the water content of the reaction product is reduced to 1 to 50 ppm or less.

The dehydration process of the present invention may be conducted in either a liquid phase or gaseous phase, but in a case of conducting the dehydration process at atmospheric pressure it is preferable to conduct the dehydration process in the gaseous phase where water is not to be solidified. Additionally, in a case of conducting it under pressure, it is preferable to perform the treatment in the liquid phase because of advantages in size, shape, throughput of a dehydration device.

Additionally, it will be understood that a process using a batch type device is possible in the process of the present invention, but a process of a continuous style is more preferable. It will be understood that an usual application style applied to an adsorption device is possible, though the objective is attained by passing a liquid or gas containing at least 1,3,3,3-tetrafluoropropene through a tubular container charged with zeolite, for instance.

Hereinafter, the second characteristic of the present invention will be discussed in detail with reference to Examples. Examples were performed at a room temperature of about 20° C., unless otherwise specified.

Preparation Example 1

A reaction tube (23 mm internal diameter, 300 mm length) formed of SUS-316 and capable of being heated with a ribbon heater was charged with 50 ml of Cr/C as a catalyst. Then, hydrogen fluoride was introduced into the reactor within a temperature range of from 200 to 400° C. at 0.2 g/min for 8 hours, thereby performing the activation of the catalyst.

Upon setting the reaction tube to have a temperature of 320° C., 1,1,1,3,3-pentafluoropropane was continuously introduced into the reactor at a rate of 0.80 g/min. Then, the reaction was continued for 10 hours thereby obtaining a reaction product.

The reaction product was subjected to sampling, followed by removing unreacted HF therefrom by absorption with a water trap for use in acid absorption. As a result of thereafter carrying out an analysis by gas chromatography, Table 4 was obtained.

TABLE 4

| Component | GC % |
|---|---|
| Trans-1,3,3,3-tetrafluoropropene | 68.21 |
| Cis-1,3,3,3-tetrafluoropropene | 14.41 |
| 1,1,1,3,3-pentafluoropropane | 17.29 |
| Others | 0.09 |

Example 1

The reaction product obtained in Preparation Example 1 was gasified by a carbureter and then used for bubbling in water at a rate of 2.19 g/min, followed by being introduced into a mist separator formed of SUS-316 and cooled by a refrigerant of 5° C. (the mist separator was previously charged with a filler formed of SUS-316). With this operation, a water content associated with the reaction product was removed. An organic substance gas was trapped at the outlet and then the water content thereof was measured by Karl Fischer's method. As a result of this, the water content was 2100 ppm. The reaction product after passing through the mist separator was passed through a dehydration tube (23 mm internal diameter, 350 mm length) charged with 100 ml of a spherical synthetic zeolite A3 having a diameter of 2 mm, at a rate of 2.19 g/min (a linear velocity of 6.0 m/min). An organic substance gas was trapped at the outlet and then the water content thereof was measured by Karl Fischer's method. As a result of this, the water content was 50 ppm. Additionally, a composition ratio of the organic substance measured by gas chromatography was equal to that of Table 4, upon which a new organic substance was not confirmed.

Preparation Example 2

The reaction product dehydrated by the process of Example 1 was distilled thereby isolating trans-1,3,3,3-tetrafluoropropene. Most of the water content was distilled out together with trans-1,3,3,3-tetrafluoropropene. The water content measured by Karl Fischer's method was 80 ppm and the purity of trans-1,3,3,3-tetrafluoropropene measured by gas chromatography was 99.9%.

Example 2

A dehydration tube formed of SUS-316 (23 mm internal diameter, 350 mm length) was charged with 100 ml of a synthetic zeolite A3 formed of a sphere having a diameter of 2 mm. Trans-1,3,3,3-tetrafluoropropene (100 ppm water content) obtained by Preparation Example 2 and having been purified was passed through the tube at a linear velocity of 1.0 m/h at 25° C. in a condition where a pressure of 0.5 MPaG was applied. The purity of trans-1,3,3,3-tetrafluoropropene was measured by gas chromatography, and the water content of the same was measured by Karl Fischer's method, at the outlet of the dehydration tube. As a result, trans-1,3,3,3-tetrafluoropropene was confirmed to have a water content of 10 ppm and a purity of 99.9%. A new organic substance was not confirmed.

The invention claimed is:

1. A process for producing 1,3,3,3-tetrafluoropropene, comprising:
   a) a first step of reacting 1,1,1,3,3-pentachloropropane with hydrogen fluoride in a liquid phase and in the absence of the fluorination catalyst, within a reaction pressure range of 0.5 to 4.2 MPa, and within a reaction temperature range of 100° C. to 160° C., thereby obtaining 1-chloro-3,3,3-trifluoropropene,
   wherein 1,1,1,3,3-pentachloropropane and hydrogen fluoride are introduced into a reaction system while hydrogen chloride and 1-chloro-3,3,3-trifluoropropene generated from the reaction are extracted from the reaction system; and
   b) a second step of reacting 1-chloro-3,3,3-trifluoropropene obtained by the first step with hydrogen fluoride in a gaseous phase and in the presence of a fluorination catalyst.

2. A process as claimed in claim 1, further comprising:
   a step of removing an excessive amount of hydrogen fluoride (HF), 1-chloro-3,3,3-trifluoropropene and 1,1,1,3,3-pentafluoropropane from a reaction mixture containing 1,3,3,3-tetrafluoropropene obtained by the second step (a step A);
   a step of further removing a remaining hydrogen fluoride (HF) after the step A (a step B); and
   a step of removing hydrogen chloride (HCl) from 1,3,3,3-tetrafluoropropene obtained by the step B (a step C).

3. A process as claimed in claim 1, wherein the fluorination catalyst used when reacting 1-chloro-3,3,3-trifluoropropene with a fluorination agent in the gaseous phase and in the presence of the fluorination catalyst (the second step) is one of: activated carbon; activated carbon that carries one of oxide, fluoride, chloride, fluorinated chloride, oxyfluoride, oxychloride and oxyfluorinated chloride of at least one kind of metals selected from chromium, titanium, aluminum, manganese, nickel, cobalt and zirconium, thereon; alumina; fluorinated alumina; aluminum fluoride; zirconia; and fluorinated zirconia.

4. A process for producing trans-1,3,3,3-tetrafluoropropene, comprising the step of:
   purifying 1,3,3,3-tetrafluoropropene obtained by the process of claim 1.

5. A process as claimed in claim 4, wherein 1-chloro-3,3,3-trifluoropropene, cis-1,3,3,3-tetrafluoropropene and 1,1,1,3,3-pentafluoropropane contained in 1,3,3,3-tetrafluoropropene, which are separated from trans-1,3,3,3-tetrafluoropropene obtained by claim 4, are used as the raw material of the second step again.

6. A process as claimed in claim 1, further comprising the step of:
   bringing 1,3,3,3-tetrafluoropropene obtained by the process of claim 1 into contact with a zeolite thereby dehydrating the 1,3,3,3-tetrafluoropropene.

7. A process as claimed in claim 6, wherein the zeolite is a zeolite belonging to Faujasite genus.

8. A process as claimed in claim 6, wherein the zeolite is a synthetic zeolite of one type of 3A, 4A, 5A, 10X and 13X.

9. A process as claimed in claim 1, further comprising:
   a step of washing the product of the first step which product comprises 1-chloro-3,3,3-trifluoropropene, with water or an alkaline aqueous solution to remove an acidic substance, followed by drying and then distillation to remove organic impurities.

10. A process as claimed in claim 2, further comprising:
    a step of bringing high boiling point contents obtained after the step A back to the second step.

11. A process as claimed in claim 2, wherein the step B further comprises one of the steps (a) to (c) to remove hydrogen fluoride (HF):
    (a) a step of reacting hydrogen fluoride with potassium fluoride or sodium fluoride to forming a complex of hydrogen fluoride, followed by reacting calcium chloride, calcium hydroxide, calcium oxide, calcium carbonate or an aqueous solution of these with hydrogen fluoride to form calcium fluoride ($CaF_2$);
    (b) a step of reacting hydrogen fluoride with sodium chloride or potassium chloride thereby forming a metal fluoride salt corresponding respectively to these to; and
    (c) a step of reacting sulfuric acid with hydrogen fluoride.

12. A process for producing 1,3,3,3-tetrafluoropropene, comprising:
    a) a first step of reacting 1,1,1,3,3-pentachloropropane with hydrogen fluoride in a liquid phase and in the absence of the fluorination catalyst within a reaction pressure range of 0.5 to 4.2 MPa and within a reaction temperature range of 100 to 160° C. thereby obtaining 1-chloro•3,3,3-trifluoropropene
    wherein 1,1,1,3,3-pentachloropropane and hydrogen fluoride are introduced into a reaction system while hydrogen chloride and 1-chloro-3,3,3-trifluoropropene generated from the reaction are extracted from the reaction system;
    b) a step of washing the product of the first step which product comprises 1-chloro-3,3,3-trifluoropropene, with water or an alkaline aqueous solution to remove an acidic substance, followed by drying and then distillation to remove organic impurities;
    c) a second step of reacting 1-chloro-3,3,3-trifluoropropene obtained by the first step with hydrogen fluoride in a gaseous phase and in the presence of a fluorination catalyst,
       wherein the fluorination catalyst is one of: activated carbon; activated carbon that carries one of oxide, fluoride, chloride, fluorinated chloride, oxyfluoride, oxychloride and oxyfluorinated chloride of at least one kind of metals selected from chromium, titanium, aluminum, manganese, nickel, cobalt and zirconium, thereon; alumina; fluorinated alumina; aluminum fluoride; zirconia; and fluorinated zirconia;
    d) a step of removing an excessive amount of hydrogen fluoride (HF), 1-chloro-3,3,3-trifluoropropene and 1,1,1,3,3-pentafluoropropane from a reaction mixture containing 1,3,3,3-tetrafluoropropene obtained by the second step (a step A);
    e) a step of further removing a remaining hydrogen fluoride (HF) after the step A (a step B); and
    f) a step of removing hydrogen chloride (HCl) from 1,3,3,3-tetrafluoropropene obtained by the step B (a step C).

13. A process as claimed in claim 12, further comprising:
    a step of bringing high boiling point contents obtained after the step A back to the second step.

14. A process as claimed in claim 12, wherein the step B further comprises one of the steps (a) to (c) to remove hydrogen fluoride (HF):
    (a) a step of reacting hydrogen fluoride with potassium fluoride or sodium fluoride to forming a complex of hydrogen fluoride, followed by reacting calcium chloride, calcium hydroxide, calcium oxide, calcium carbonate or an aqueous solution of these with hydrogen fluoride to form calcium fluoride ($CaF_2$);
    (b) a step of reacting hydrogen fluoride with sodium chloride or potassium chloride thereby forming a metal fluoride salt corresponding respectively to these to; and
    (c) a step of reacting sulfuric acid with hydrogen fluoride.

* * * * *